US008870784B2

(12) United States Patent
Blandin et al.

(10) Patent No.: US 8,870,784 B2
(45) Date of Patent: Oct. 28, 2014

(54) PRECISION OF XENON CONTENT MEASUREMENT IN A VENTILATORY ANESTHESIA APPARATUS

(75) Inventors: Richard Blandin, Paris (FR); Bernard Cariou, Montigny le Bretonneux (FR); Christian Daviet, Paris (FR); Sophie Dussud, Rueil Malmaison (FR); Noureddine Kissi, Meudon la Foret (FR)

(73) Assignee: L'Air Liquide, Societe Anonyme pour l'Etude et l'Exploitation des Procedes Georges Claude, Paris (FR)

( * ) Notice: Subject to any disclaimer, the term of this patent is extended or adjusted under 35 U.S.C. 154(b) by 1004 days.

(21) Appl. No.: 12/994,022
(22) PCT Filed: May 12, 2009
(86) PCT No.: PCT/FR2009/050859
§ 371 (c)(1),
(2), (4) Date: Jan. 11, 2011
(87) PCT Pub. No.: WO2009/153468
PCT Pub. Date: Dec. 23, 2009

(65) Prior Publication Data
US 2011/0105934 A1 May 5, 2011

(30) Foreign Application Priority Data
May 27, 2008 (FR) .................................... 08 53430

(51) Int. Cl.
A61B 5/08 (2006.01)
(Continued)

(52) U.S. Cl.
CPC ....... *A61M 16/104* (2013.01); *A61M 2016/103* (2013.01); *A61M 16/01* (2013.01);
(Continued)

(58) Field of Classification Search
USPC ......................... 128/203.12, 204.22; 600/532
See application file for complete search history.

(56) References Cited

U.S. PATENT DOCUMENTS

| 4,903,693 A | | 2/1990 | Yasue |
| 4,989,597 A | * | 2/1991 | Werner .................... 128/203.12 |

(Continued)

FOREIGN PATENT DOCUMENTS

| DE | 37 42 880 | 3/1989 |
| DE | 296 13 243 | 10/1996 |

(Continued)

OTHER PUBLICATIONS

International Search Report for related PCT/FR2009/050859, Oct. 16, 2009.

(Continued)

*Primary Examiner* — Navin Natnithithadha
*Assistant Examiner* — Meredith Weare
(74) *Attorney, Agent, or Firm* — Allen E. White

(57) ABSTRACT

The invention relates to an apparatus for the ventilatory anaesthesia of a patient by administration of a gas containing gaseous xenon that comprises a main gas circuit (CP) and a means for determining the xenon content (S6, M1) adapted for and capable of determining the gaseous xenon content in the main circuit (CP), and comprising at least one hot wire sensor (S6-E) including at least one electrically conducting wire (FC1) in direct contact with at least a portion of the xenon-containing gaseous flow. At least one hot wire sensor (S6-E) including at least one conducting wire (FC1) is arranged on a gas-supply main line (LP) including a bypass line (BP) fluidically connected to said gas-supply main line (LP) upstream and downstream from said at least one conducting wire (FC1) and taking into account the gas flow direction in said main line (LP), and at least a first electrovalve (EV1) is provided at the upstream connection of the bypass line (BP) to said main line (LP) in order to direct the xenon-containing gaseous flow either towards the main line (LP) on which said at least one conducting wire (FC1) is provided, or towards the bypass line (BP).

22 Claims, 6 Drawing Sheets

(51) Int. Cl.
*A61M 16/01* (2006.01)
*A61M 16/10* (2006.01)
*A61M 16/20* (2006.01)
*A61M 16/12* (2006.01)
*G01N 33/00* (2006.01)
*A61M 16/00* (2006.01)
*A61M 16/22* (2006.01)
*A61M 16/08* (2006.01)

(52) U.S. Cl.
CPC . *A61M 2230/435* (2013.01); *A61M 2016/0039* (2013.01); *A61M 2016/0042* (2013.01); *A61M 16/205* (2013.01); *A61M 2016/1025* (2013.01); *A61M 2205/70* (2013.01); *A61M 16/22* (2013.01); *A61M 2016/1035* (2013.01); *A61M 16/12* (2013.01); *A61M 16/0081* (2013.01); *A61M 2230/432* (2013.01); *A61M 16/0808* (2013.01); *A61M 2202/0291* (2013.01); *A61M 16/085* (2013.01); *A61M 16/0078* (2013.01); *A61M 2230/437* (2013.01); *G01N 33/0036* (2013.01)
USPC .. 600/532; 600/529; 128/204.22; 128/204.23

(56) References Cited

U.S. PATENT DOCUMENTS

| | | | | |
|---|---|---|---|---|
| 5,558,083 | A | * | 9/1996 | Bathe et al. ............... 128/203.12 |
| 6,095,137 | A | * | 8/2000 | Wallroth et al. ......... 128/203.26 |
| 7,703,455 | B2 | | 4/2010 | Bunke et al. |
| 8,141,552 | B2 | * | 3/2012 | Daviet et al. ............. 128/203.12 |
| 2001/0022181 | A1 | | 9/2001 | Masson et al. |
| 2003/0216660 | A1 | * | 11/2003 | Ben-Oren et al. ............ 600/532 |
| 2009/0090359 | A1 | * | 4/2009 | Daviet et al. ............. 128/203.14 |

FOREIGN PATENT DOCUMENTS

| | | | |
|---|---|---|---|
| EP | 0 523 315 | 1/1993 | |
| EP | 0 983 771 | 3/2000 | |
| EP | 1 120 126 | 8/2001 | |
| EP | 1 318 797 | 3/2002 | |
| FR | 2 862 227 | 5/2005 | |
| WO | 1 499 377 | 11/2003 | |
| WO | WO 2004 024053 | 3/2004 | |
| WO | WO 2007 068849 | 6/2007 | |
| WO | WO-2007068849 A2 * | 6/2007 | ............ A61M 16/01 |

OTHER PUBLICATIONS

Written Opinion for related PCT/FR2009/050859, Oct. 16, 2009.
French Search Report for related FR 08 53430, Jan. 22, 2009.

* cited by examiner

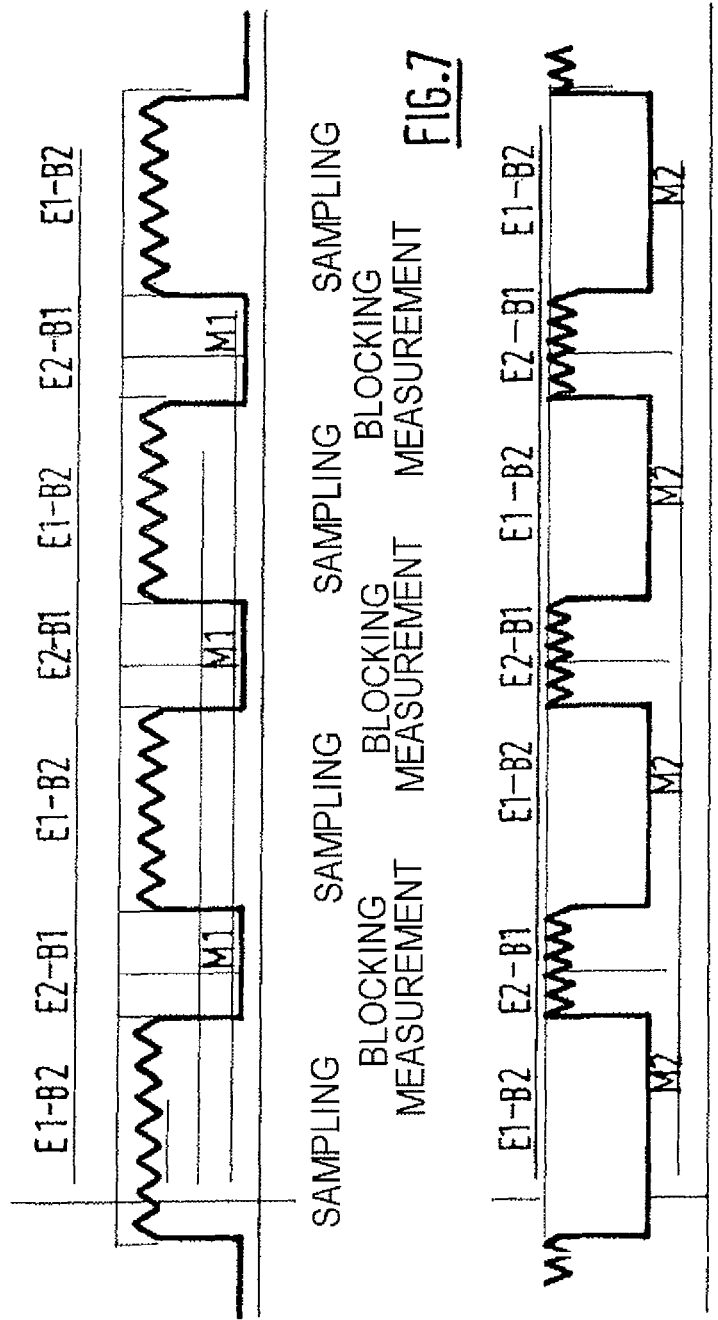

PRECISION OF XENON CONTENT MEASUREMENT IN A VENTILATORY ANESTHESIA APPARATUS

This application is a 371 of International PCT Application PCT/FR20091050859, filed May 12, 2009, the entire contents of which are incorporated herein by reference.

FIELD OF THE INVENTION

The present invention relates to an apparatus for ventilatory anesthesia by administration of gaseous xenon to the airways of a patient, said apparatus being provided with a device for measuring the concentration of xenon and allowing good measurement precision.

BACKGROUND

Many ventilatory anesthesia apparatuses are known that can be used to perform anesthesia on a patient who is to undergo a surgical intervention or similar, by administering to the patient, by inhalation, a conventional anesthetic gaseous mixture composed of $N_2O$, halogenated agents, for example sevoflurane, isoflurane, desflurane, etc. In this connection, reference may be made to documents EP-A-983 771 and EPA-A-1 120 126.

Xenon is an anesthetic gas that has been known since the start of the 1950s and that is being used more and more in the medical field, especially as it is particularly suitable for anesthesia of weak patients (elderly patients, long operations, cardiac surgery, neurosurgery, etc.), in particular because of the virtual absence of any influence on blood pressure during anesthesia and the virtual absence of side effects or adverse events.

However, anesthesia performed with xenon requires monitoring of the concentrations of xenon in the gaseous flow administered to the patient, that is to say requires that the concentration of xenon in the anesthetic flow can be determined in real time. In this connection, reference may be made, for example, to documents EP-A-1 499 377, EP-A-1 318 797 or EP-A 523 315.

To measure the concentration of xenon in such a gaseous mixture, it is customary to use a mass spectrometer or a chromatograph. These techniques, however, have disadvantages as regards cost and especially as regards the difficulty of implementing them, since their integration in existing anesthesia apparatuses requires considerable efforts in terms of development and adaptation.

An alternative has been proposed in WO-A-2007/068849, which discloses an apparatus for ventilatory anesthesia of a patient by administration of a gas containing gaseous xenon, said apparatus comprising means for determining the xenon concentration so as to determine the content of gaseous xenon in the main gas circuit in the form of an open or closed circuit.

In this apparatus, one or more hot-wire sensors, each having at least one wire made of electrically conductive material, preferably metal, are in direct contact with the gaseous flow containing the xenon, and calculating means cooperate with the hot-wire sensor(s) in such a way as to determine the concentration of xenon in said gaseous flow from a voltage measurement carried out by the voltage-measuring means at the terminals of at least one hot wire or of a resistance placed in series with at least one hot wire, when said at least one hot wire is in contact with the gaseous flow and is traversed by an electric current.

Although this apparatus makes it possible to determine with sufficient precision the concentration of xenon delivered to the patient during gas anesthesia in such a way as to guarantee efficacy of anesthesia and increased safety for the patient, while at the same time being of simple architecture of modest cost, it has been found in practice that, in certain cases, especially in the case of the onset of occlusion that can occur during the course of use through accumulation of humidity in the sampling line or in the case of normal or premature aging of the suction pump, the stability of the measured signal or signals may be adversely affected by the fluctuations in the capacity of the pump for removing the samples.

The reason for this is that, when the sample of gas to be measured is susceptible to variations in flowrate or fluidic oscillations, due for example to the pump for removing the gaseous sample, this is to some extent manifested in disturbances in the measurement of the concentration of xenon.

Although these disturbances lead to a concentration measurement that remains very acceptable, it is desirable to be able to eliminate these disturbances and avoid these fluctuations in the measurement of the content of xenon.

In other words, the problem to be solved is that of improving the apparatus described in WO-A-2007/068849 in such a way as to eliminate all the disturbances in the measurement of the concentration of xenon in the gaseous flow and thereby increase the measurement stability, that is to say provide this device with greater measurement precision, so as to be able to achieve even more effective, reliable and precise monitoring of the concentrations of gaseous xenon in a gaseous anesthesia mixture based on xenon containing, in addition, and in variable quantity, that is to say from 0 to 100% by volume, one or more of the following main compounds: oxygen ($O_2$), nitrogen ($N_2$), nitrous oxide ($N_2O$), carbon dioxide ($CO_2$), halogenated compounds of the isoflurane, enflurane, desflurane, sevoflurane or halothane type, ethanol, and, optionally, traces or small quantities (<1%) of one or more of the following minor compounds: acetone, methane, carbon monoxide (CO), argon, helium, etc.

SUMMARY OF THE INVENTION

To this end, the invention proposes an apparatus for ventilatory anesthesia of a patient by administration of a gas containing gaseous xenon, said apparatus comprising:
- a main gas circuit in the form of an open or closed circuit having an inhalation branch for supplying a gaseous mixture containing xenon to the patient and an exhalation branch for conveying the gaseous mixture containing xenon exhaled by the patient, and
- means for determining the concentration of xenon, which are designed and able to determine the gaseous xenon content in at least part of the main circuit, said means for determining the concentration of xenon comprising at least one hot-wire sensor having at least one electrically conductive wire in direct contact with at least part of the gaseous flow containing the xenon, characterized in that
- at least one hot-wire sensor having at least one conductive wire is arranged on a gas-supply main line having a bypass line connected fluidically to said gas-supply main line upstream and downstream from said at least one conductive wire, as seen in the direction of circulation of the gas in the main line, and
- at least a first solenoid valve is arranged in the area of the upstream connection of the bypass line to said main line in such a way as to direct the gaseous flow containing the xenon either to the main line, on which said at least one conductive wire is arranged, or to the bypass line.

BRIEF DESCRIPTION OF THE FIGURES

FIG. 7 is a graph showing gas flowrate.
FIG. 8 is a graph showing gas flowrate.

DETAILED DESCRIPTION OF THE INVENTION

Figure 1:
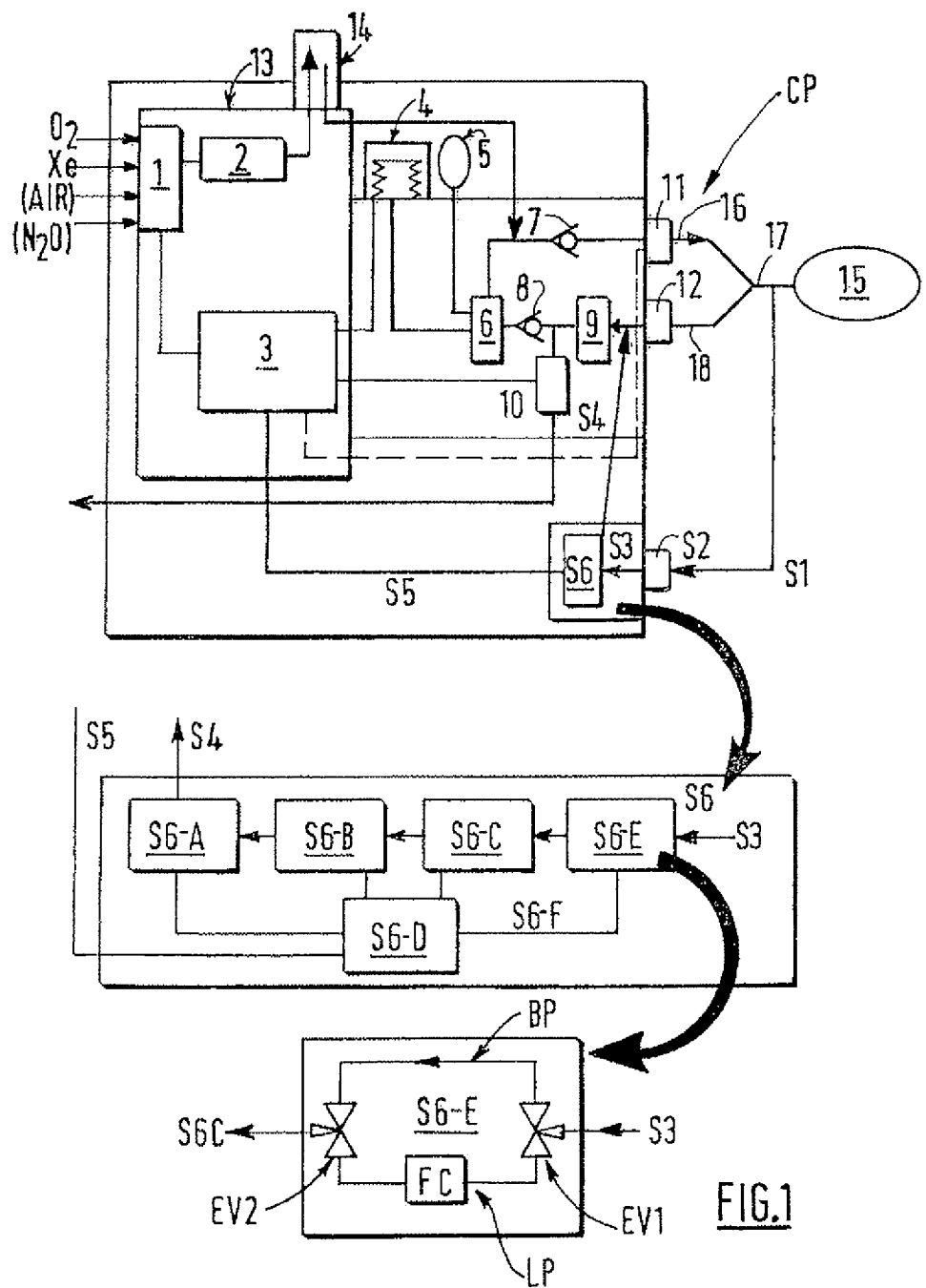
FIG. 1 illustrates a first embodiment of an apparatus according to the present invention.

Depending on the circumstances, the apparatus of the invention can comprise one or more of the following features:
  the gas-supply main line and the bypass line are ramifications of a bypass line communicating fluidically with the main circuit, and at least a first solenoid valve is arranged at the intersection of said bypass line, the gas-supply main line and the bypass line, and the connection of the bypass line to the main circuit is preferably made on the inhalation branch and/or on the exhalation branch and/or at a site located in immediate proximity to the patient's mouth, more preferably in the area of a connection site between the inhalation branch and the exhalation branch of said main circuit, for example in the area of a Y-shaped connector piece or of a bacteriological filter arranged on the main circuit;
  at least one hot-wire sensor is arranged directly on the inhalation or exhalation branch of the main circuit, and the gas-supply main line and the bypass line are ramifications of the inhalation or exhalation branch of the main circuit, and at least a first solenoid valve is arranged at the intersection of the inhalation or exhalation branch, the main line and the bypass line;
  at least a second solenoid valve is arranged in the area of the downstream connection of the bypass line to said main line;
  at least one nonreturn valve is arranged on the gas-supply main line, between at least one conductive wire and the downstream connection of the bypass line to said main line;
  at least a second sensor with conductive wire is arranged on the bypass line and measures the xenon concentration, for example during the exhalation phase, while at least one conductive wire measures the concentration during the inhalation phase, or vice versa;
  at least one hot-wire sensor is arranged on the inhalation branch, upstream or downstream from the inhalation flowrate sensor, so as to permit measurement of the inhaled fraction of xenon;
  at least one hot-wire sensor is arranged on the exhalation branch, upstream or downstream from the exhalation flowrate sensor, so as to permit measurement of the exhaled fraction of xenon;
  the solenoid valves are controlled by control means or by an independent interface;
  it comprises means for supplying gaseous xenon, which are connected to the main circuit in order to supply the inhalation branch of the main circuit with a gas containing xenon, and calculating means cooperating with at least one hot-wire sensor in such a way as to determine the concentration of xenon in said gaseous flow, means for generating electric current, which means are able and designed to generate an electric current in at least one hot wire of said at least one hot-wire sensor, voltage-measuring means which are able to measure at least one voltage value at the terminals of at least one hot wire of said at least one hot-wire sensor or at the terminals of at least one resistance arranged in series with at least one hot wire of said at least one hot-wire sensor, when said at least one hot wire is in contact with the gaseous flow and is traversed by an electric current of non-zero intensity, and the calculating means cooperate with the voltage-measuring means in such a way as to determine, from the voltage measurement carried out by said voltage-measuring means, the concentration of xenon in said flow.

The invention also relates to a method for performing anesthesia on a patient, in which method an inhalation gas containing xenon is administered into the upper airways of the patient in such a way as to perform gas anesthesia of said patient, and the xenon content of the gas administered to the patient is determined by means of an anesthesia apparatus according to the invention.

The function of the apparatus of the present invention is therefore based on the use of one or more hot-wire sensors for determining, in real time, the instantaneous and/or mean concentration of xenon present in the anesthetic gas in the inhalation phase and/or in the exhalation phase. The invention also makes it possible to provide the concentration of the inhaled and/or exhaled xenon gas.

The principle of measuring the flowrate of an anesthetic gas by means of one or more hot-wire sensors is given in document WO-A-2007/068849, to which reference may be made for further details, especially regarding the manner of calculating the concentration of xenon from the voltage value (s) measured at the terminals of the hot wire(s) or of a resistance placed in series with at least one hot wire, when the hot wire in question is in contact with the gaseous flow containing the xenon and is traversed by an electric current of non-zero intensity.

The invention will be better understood from the following description made with reference to the attached figures, in which:

FIG. 1 shows a first embodiment of an apparatus according to the invention, and

Figure 2:
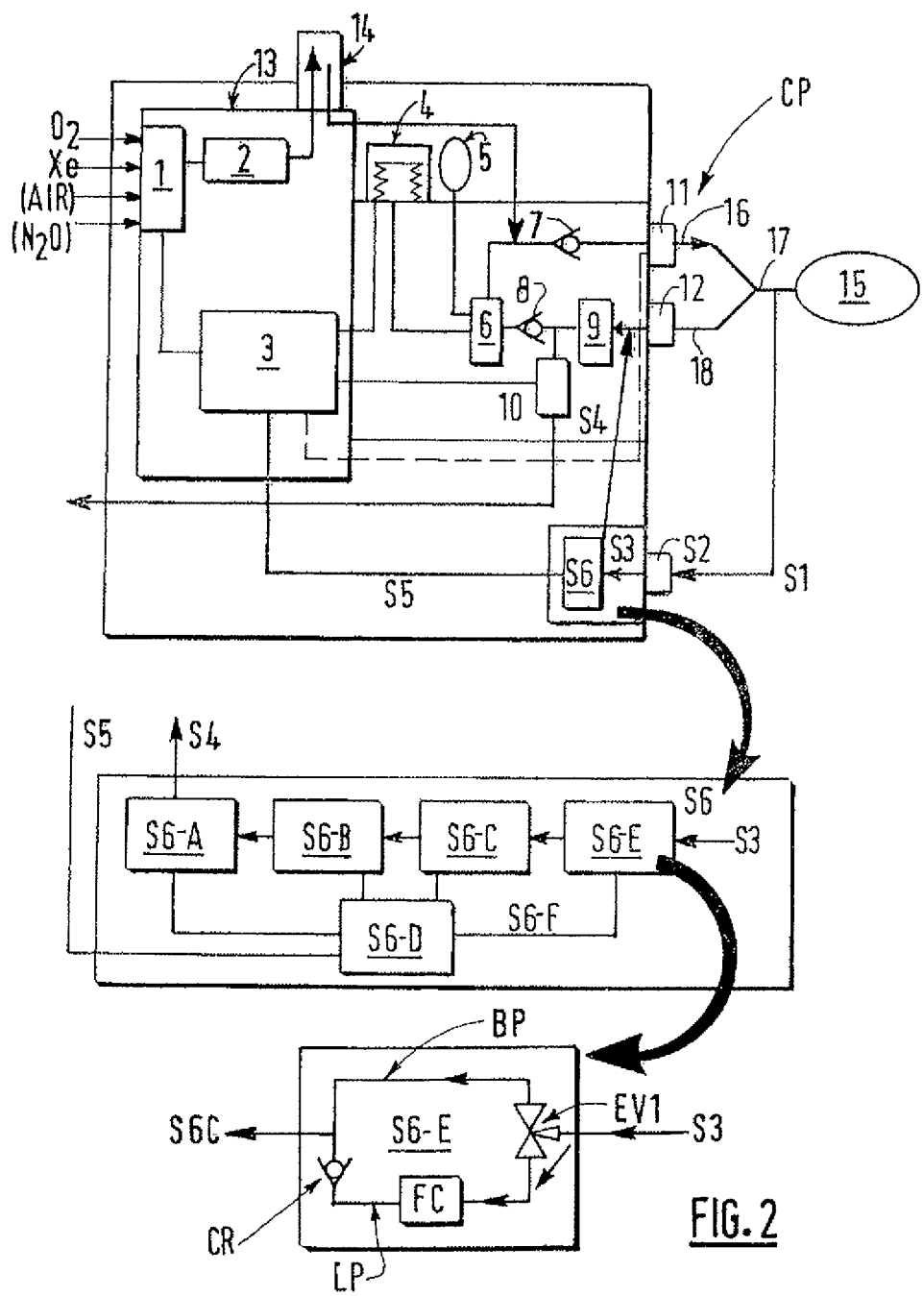
FIG. 2 illustrates a variant of the first embodiment of the apparatus in FIG. 1.
Figure 3:
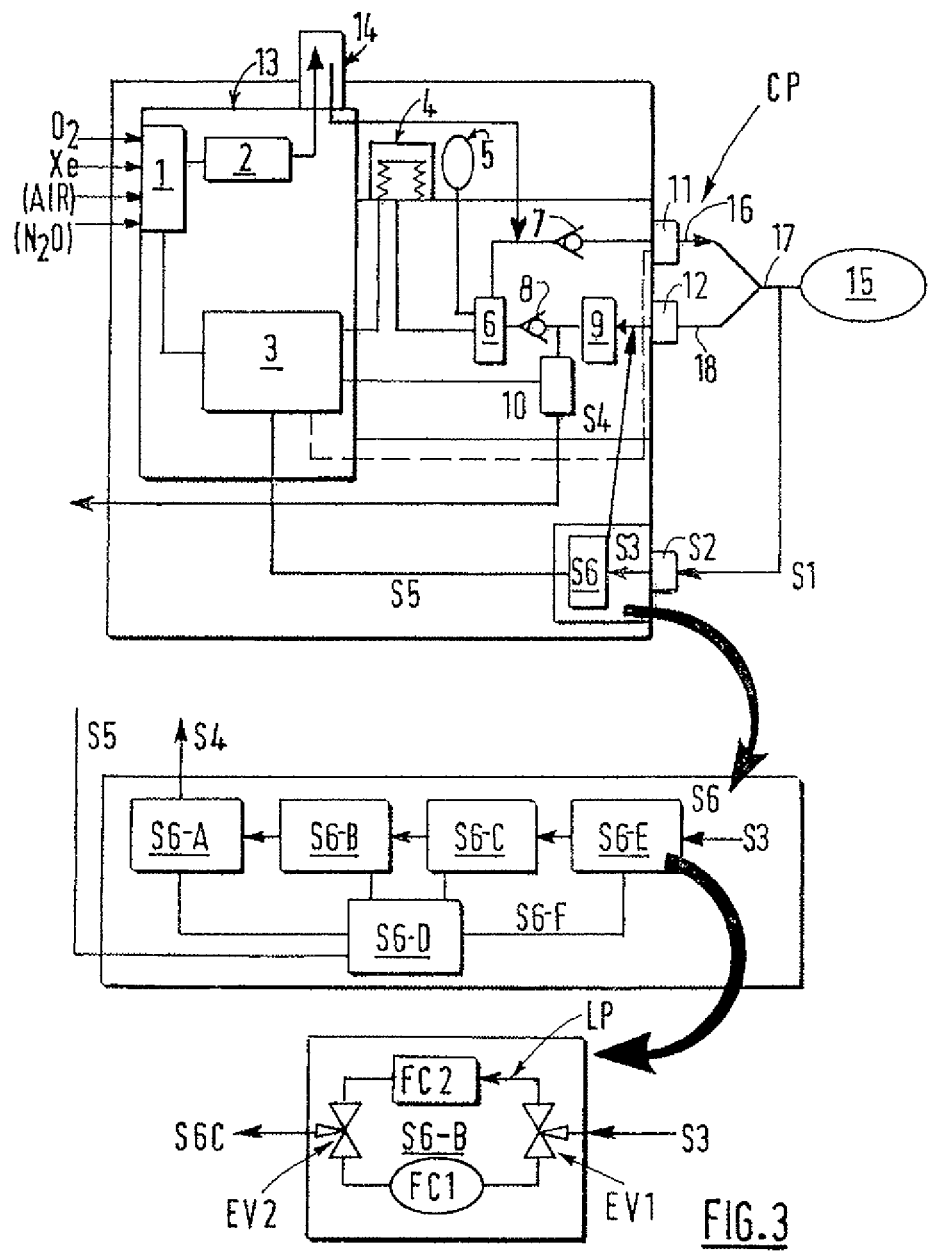
FIG. 3 illustrates another variant of the first embodiment of the apparatus in FIG. 1.
Figure 4:
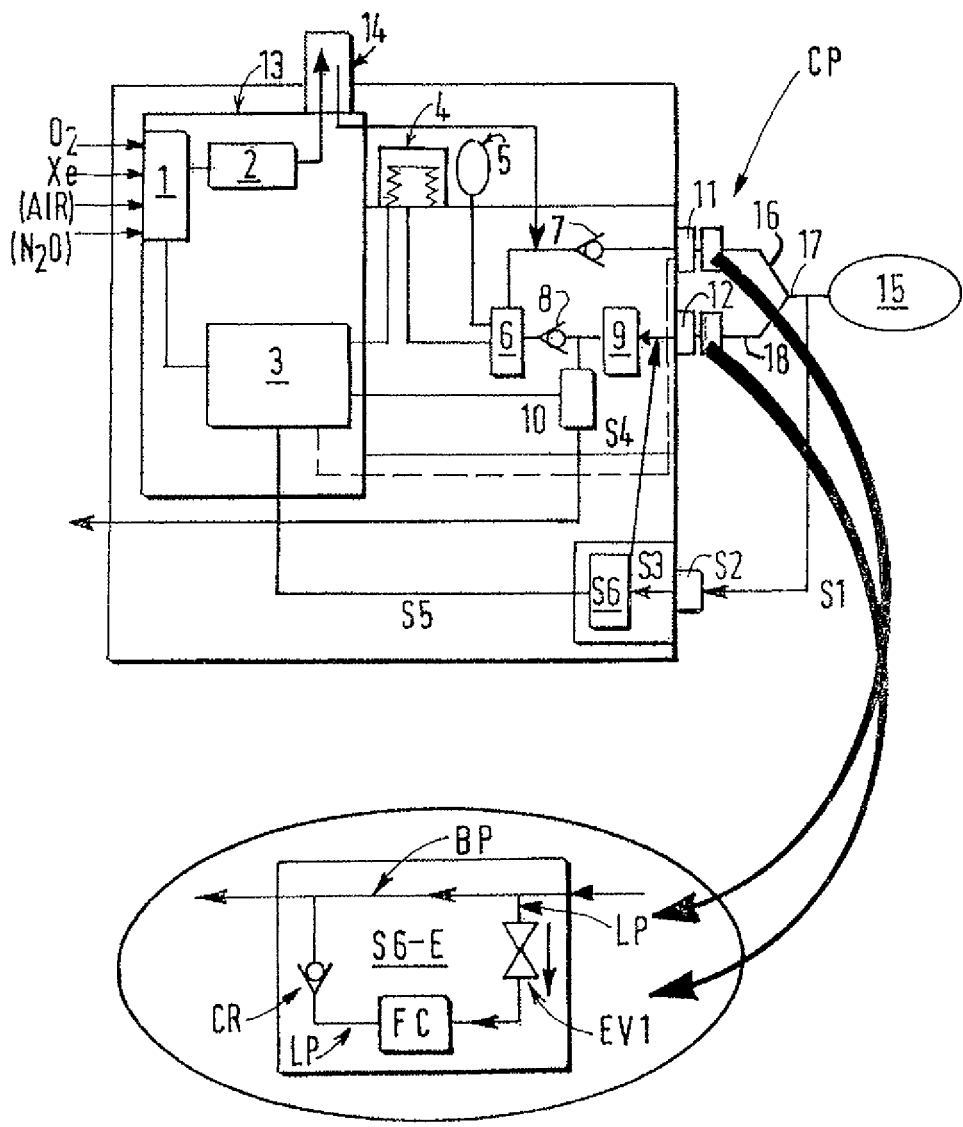
FIG. 4 illustrates a second embodiment of an apparatus according to the present invention.

FIGS. 2 and 3 show variants of the embodiment of the apparatus in FIG. 1,

FIG. 4 shows a second embodiment of an apparatus according to the invention, and FIGS. 5 to 8 are graphs showing gas flowrate.

FIGS. 1 to 4 illustrate an anesthesia apparatus according to the invention having in common, regardless of the embodiment considered; the same reference signs and the same terminology will therefore be used to designate identical parts or elements.

The apparatus or ventilator in FIGS. 1 to 4 comprises an inlet unit 1 having connection means to which are connected the source of xenon and the other sources of gases supplying the anesthesia apparatus, such as gas bottles or a wall system, in particular for the sources of air (AIR), oxygen ($O_2$) and/or nitrous oxide ($N_2O$).

This unit 1 is in fluidic communication with the inlet of a mixer 2 where the xenon is mixed with the other gas or gases intended to form the anesthetic gaseous mixture, in particular oxygen in a quantity sufficient for the patient (non-hypoxic), and the outlet of the mixer 2 supplies gaseous mixture to a vessel 14 for halogenated compounds, which is mounted on a vessel support 13 and contains a halogenated compound designed to be entrained by the flow of anesthetic gas to the patient 15.

The halogenated gaseous mixture leaving the vessel 14 is introduced into a main circuit CP or patient circuit having an inhalation branch 16 for supplying the gaseous mixture to the patient 15 and an exhalation branch 18 for recovering all or some of the gas exhaled (charged with $CO_2$) by the patient 15. The inhalation 16 and exhalation 18 branches form a loop circuit or closed circuit. The inhalation 16 and exhalation 18 branches are connected to the patient 15 by, for example, a Y-shaped piece 17 and a respiratory mask, a tracheal tube or the like.

Inhalation 7 and exhalation 8 nonreturn valves are preferably provided, respectively, on said inhalation 16 and exhalation 18 branches. The exhalation branch 18 has a $CO_2$ absorber 9 comprising a vessel filled with an absorbent material, such as lime, making it possible to remove the $CO_2$ exhaled by the patient 15 and conveyed by the exhaled gas in the exhalation branch 18 of the main circuit, and also an exhaust valve 10 making it possible to evacuate any surplus of gas and/or any excess gas pressure in the exhalation branch 18.

Moreover, the ventilator of the invention includes, in a manner known per se, a mechanical ventilation bellows 4 incorporated in an enclosure, and also a manual ventilation balloon 5, which are able to be selectively connected fluidically to the main circuit CP in order to supply the latter with gas under pressure, via a bellows/balloon selector 6.

Control means 3 comprising, for example, at least one electronic control card and one or more on-board pieces of software or computer programs make it possible to collect at least some of the information or signals coming from all or some of the sensors of the apparatus and to process them and/or to carry out all the calculations needed for monitoring the concentrations of gas and/or for controlling the various elements of the apparatus.

In particular, an inhalation flowrate sensor 11 and an exhalation flowrate sensor 12, arranged respectively on the inhalation 16 and exhalation 18 branches of the main circuit (CP), measure the inhalation and exhalation flowrates in said branches and transmit the measurement signals thus obtained to the control means 3 via suitable electrical connections. In this way, the control means 3 are able to control the bellows 4 and/or the opening of the exhaust valve 10 and/or the intake of the appropriate gases in the inlet unit 1 to which said control means 3 are connected via dedicated electrical connections, as can be seen in FIG. 1.

In order to be able to carry out a measurement and effective monitoring of the xenon content of the gaseous mixture, the apparatus of the invention incorporates a gas analysis module S6 called a "gas bench" having one or more hot-wire sensors swept by a diverted gaseous flow. The gas analysis module S6 is shown in an enlarged and detailed manner in FIG. 1, at the end of the curved arrow.

More precisely, some of the gas flow based on xenon and conveyed through the main gas circuit CP is drawn off, in the area of the Y-shaped piece 17, via a sampling line S1 that communicates fluidically with said main circuit CP.

The line S1 conveys the anesthetic gas to the module S6, first causing the gas to pass through a water trap S2 where the water vapor it contains is removed, before the gas is conveyed, via a transfer line S3, to the gas analysis module S6.

For its part, the gas analysis module S6 comprises, arranged on the passage of the flow of gas:

- a suction pump S6-A, for example of the type fitted to the gas benches BGA4800 or BGA4700 from the Andros company or to the AION from the Artema company, for creating a known suction flowrate of anesthetic gas,
- a hot-wire sensor S6-E consisting, in this example, of a single platinum wire, traversed by an electric current of given intensity (I), for example an intensity of approximately 100 mA, with measurement of the voltage at the terminals of said wire when the latter is in contact with the flow containing the xenon, for example a hot-wire sensor from the Taema company, permitting measurement of the concentration of xenon,
- an infrared cell S6-B, for example of the type fitted to the abovementioned gas benches BGA4800 or BGA4700, making it possible to measure the instantaneous and/or mean and/or inhaled and/or exhaled concentrations of $CO_2$, $N_2O$, halogenated compounds, ethanol, or any other gas that can be measured by this infrared technology,
- a cell paramagnetic to $O_2$ or a chemical battery S6-C, for example of the type fitted to the above-mentioned gas benches BGA4800 or BGA4700, in order to measure the instantaneous and/or mean and/or inhaled and/or exhaled concentrations of $O_2$,
- control means S6-D with software integrated on an electronic control card, for example of the type fitted to the abovementioned gas benches BGA4800 or BGA4700,
- suitable connections connecting the infrared cell S6-B and the oxygen cell S6-C to the control means S6-D.

The outlet of the suction pump S6-A of the module S6 is connected to the exhalation branch of the main circuit, via a re-injection line S4, in such a way as to return thereto the gas that has been withdrawn from it via the sampling line S1.

Moreover, as is shown, the measurement signals obtained with the hot-wire sensor S6-E are transmitted to the control means S6-D via a suitable connection S6-F, said control means S6-D being themselves connected to the control means 3 via a suitable electrical connection S5.

The calculations, particularly of xenon concentrations of the anesthetic gas, are performed by the control means S6-D of the module S6.

This gas analysis module S6 thus makes it possible to perform all the desired measurements on the gas suctioned through the sampling line S1 at a continuous flowrate.

It should be noted that the hot-wire sensor S6-E, although shown at the inlet of the module S6 and upstream from the cell S6-C, can also be inserted elsewhere, in particular downstream from the suction pump S6-A and/or upstream from or on the re-injection line S4, the latter being optionally connected to the main circuit.

The hot-wire sensor S6-E performs, in real time, the measurement of the voltage generated at the terminals of the hot wire by the aspirated gas and transmits the measurement via the connection S6-F, with a known and more or less short delay of a few tens or even a few hundreds of ms depending on the regulated aspiration flowrate, to the control software S6-D of the anesthetic gas analyzer, such that the latter deduces therefrom a real-time measurement of the xenon content (Xe %), of the inhaled fraction of xenon (FiXe) or of the exhaled fraction of xenon (FeXe), or even a mean concentration of xenon, as is explained in WO-A-2007/068849.

FIGS. 1 to 4 show several embodiments of an apparatus according to the invention comprising means for carrying out a more precise measurement of the concentration of xenon.

Thus, as is illustrated in FIGS. 1 to 3, the invention is based on the incorporation, in the area of the hot-wire sensor S6-E, of one or more solenoid valves EV1, EV2 arranged upstream and possibly downstream from said hot-wire sensor S6-E. Indeed, said solenoid valve or two solenoid valves EV1, EV2 make it possible to:

control the supply of the gaseous sample to the measuring device by sampling and/or suction by the pump, for example of the module S6, to interrupt the circulation of the gaseous sample to be measured in a part of the device where a hot wire FC is located, by allowing the sampling flowrate to flow through a fluid line or bypass line BP which is situated in parallel with the main line LP on which the measuring device is located, that is to say the hot wire FC, as is shown in FIGS. 1 and 2, allowing the calculator to perform the measurement of the concentration of xenon in the gas for a given time during which the sample to be measured is at zero flowrate, since the solenoid valve EV1 is closed. At the end of this measurement time, the gaseous sample whose principle is based on the sampler-blocker (as explained below) continues its normal path through the measuring device, that is to say from EV1 to EV2 (in FIG. 1 for example). During the time that the measurement is carried out, the gaseous sample must not be interrupted, it is conveyed through the bypass line BP, which is situated in parallel with the measuring device.

Figure 5:
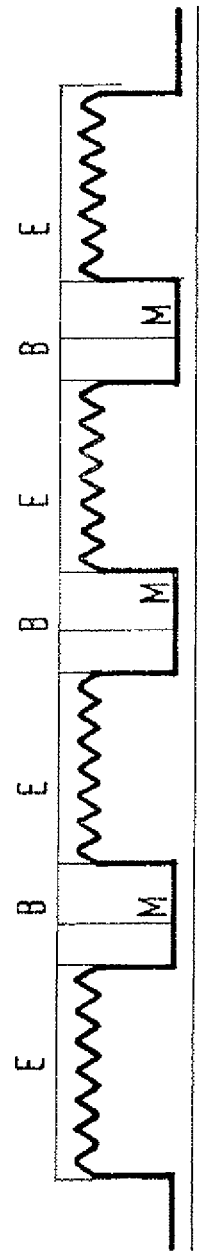
FIG. 5 is a graph showing gas flowrate.
Figure 6:
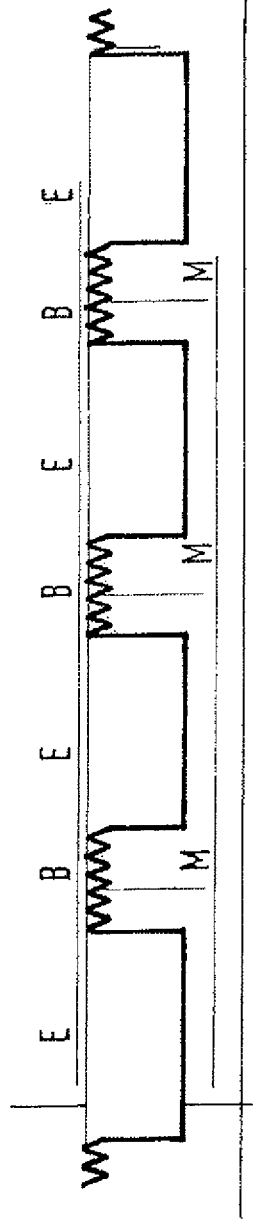
FIG. 6 is a graph showing gas flowrate.

The principle by which xenon is measured in the embodiment in FIGS. 1 and 2 is in fact based on that of the sampler-blocker, as is illustrated in the timing diagrams of FIG. 5, which shows the gas flowrate seen by the hot-wire sensor FC used for measuring the xenon concentration, and of FIG. 6, which illustrates the gas flowrate passing through the bypass line BP which is arranged in parallel with the chamber situated on the main line LP and containing the hot-wire sensor FC used to measure the xenon concentration.

During the phase called "Sampling" (E), the sampling flowrate is oriented by the solenoid valve EV1, via the main line LP, to pass through the chamber where the hot wire FC is arranged. During this phase, the amplitude of the electrical signal is measured at the terminals of the hot wire during the sampling phase in order to verify that the flowrate passes through and thus to guarantee that the next measurement M will be coherent.

During the phase called "Blocking" (B), the sampling flowrate is oriented by the solenoid valve EV1 to the bypass line BP such that the gas to be measured is stored in the cell FC formed by the flowrate sensor isolated between EV1 and EV2 (in FIG. 1) or between EV1 and CR (in FIGS. 2 and 4) and is at zero flowrate. During the second part of the blocking phase, the measurement of the xenon concentration is carried out as explained in WO-A-97/068849, deducing the xenon concentration from the measurement of the voltage at the terminals of the hot wire by using, from among the system of straight lines V=f(débit) (Xe), the straight line corresponding to a zero flowrate. It is thus also possible to calculate the mean concentration of xenon in the sampled gas by averaging the measurements.

Optionally, it is also possible to synchronize the sampling and blocking phases, for example to the measurement of $CO_2$ or measurement of the pressure, in such a way that the sampling phase E is synchronized with the insufflation phase and the blocking phase B is synchronized with the exhalation phase of the patient, the measurement M then corresponding to the inhaled fraction of xenon, or in such a way that the sampling phase E is synchronized with the exhalation phase and the blocking phase B is synchronized with the insufflation phase, the measurement M then corresponding to the exhaled fraction of xenon.

It should be noted that the major difference between FIGS. 1 and 2 lies in the presence, in the embodiment in FIG. 1, of two solenoid valves EV1 and EV2 situated upstream and downstream from the hot wire FC, whereas in the embodiment in FIG. 2 only one solenoid valve EV1 is arranged upstream from the hot wire, and a nonreturn valve CR has been arranged downstream from said hot wire FC, on the gas-supply main line LP.

Moreover, FIG. 3 shows another variant of the embodiment from FIG. 1, the measurement being based on the principle of a double sampler-blocker (see timing diagrams in FIGS. 7 and 8) making it possible to measure the xenon concentration continuously. In this case, two hot-wire sensors are used to measure the xenon content, namely a first hot-wire sensor FC1 and a second hot-wire sensor FC2, both sensors being clearly distinct and being able to each have one or more hot wires.

More precisely, as before, FIG. 7 shows the flowrate seen by the hot-wire sensor FC1 used to measure the xenon concentration, whereas FIG. 8 illustrates the flowrate seen by the hot-wire sensor FC2 used to measure the xenon concentration.

During the phase called Sampling 1-Blocking 2 (E1-B2), the sampling flowrate is oriented to pass through the first hot wire FC1, whereas the preceding sample is at zero flowrate in the chamber containing the second hot wire FC2. During this phase, the amplitude of the electrical signal is estimated measured at the terminals of the first hot wire FC1 during the sampling phase in order to verify that the flowrate passes through and thereby to guarantee that the next measurement (M1) will be coherent. During this phase, the measurement (M2) of the xenon concentration of the sample blocked in the chamber containing the second hot wire FC2 is also carried out by using, from among the system of straight lines V=f (débit) (Xe), the straight line corresponding to the zero flow rate.

During the phase called Sampling 2-Blocking 1 (E2-B1), the sampling flowrate is oriented to pass through the second hot wire FC2, whereas the preceding sample is at zero flowrate in the chamber containing the hot wire FC1. During this phase, the amplitude of the electrical signal is measured at the terminals of the first hot wire FC2 during the sampling phase in order to verify that the flowrate passes through and to thereby guarantee that the next measurement (M2) will be coherent. During this phase, the measurement (M1) of the xenon concentration of the sample blocked in the chamber containing the first hot wire FC1 is also measured by using, from among the system of straight lines V=f(débit) (Xe), the straight line corresponding to the zero flowrate, as is explained above.

It is thus possible, if so required, to calculate the mean concentration of xenon in the sampled gas by averaging the measurements M1 and M2.

Optionally, as before, it is also possible to synchronize the sampling and blocking phases, by S6-D, for example to the $CO_2$ cycles detected by S6-C, in such a way that on one of the hot-wire sensors (FC1 for example), the Sampling phase is synchronized with the insufflation phase and the Blocking phase is synchronized with the exhalation phase, the measurement M1 then corresponding to the inhaled fraction of xenon, and in such a way that on the other hot-wire sensor (FC2 for example) the Sampling phase is synchronized with the exhalation phase and the Blocking phase is synchronized with the insufflation phase, the measurement M2 then corresponding to the exhaled fraction of xenon.

In other words, FIG. 1 uses two solenoid valves 3/2 (3 to 2) upstream EV1 and downstream EV2 from the device for measuring the xenon concentration comprising the hot wire FC. These solenoid valves switch simultaneously in order to pass the gaseous sample either through the device for measuring the concentration or through the bypass line BP while the device carries out the measurement of the concentration at zero flowrate.

By contrast, FIG. 2 uses only a single solenoid valve EV1 situated upstream from the hot wire FC in order to direct the gaseous sample either through the device for measuring the concentration or through the bypass line BP. In this case, a nonreturn valve CR is situated downstream from the hot wire FC in order to avoid any return of gas to the hot wire.

The device S6E is situated in series with the different sensors S6C, S6B, S6A which compose the gas bench; it can be placed at the start or at the end of the chain, and is independent of the other sensors.

FIG. 4 illustrates a second embodiment in which a hot-wire sensor S6-E similar to that in FIG. 2, or even to that in FIG. 1, is positioned in series upstream or downstream from the inhalation flowrate sensor 11 and can in this way permit measurement of the inhaled fraction of xenon by synchronizing the blocking phase with the exhalation phase by detecting the disappearance of a positive insufflation pressure or by detecting an exhalation flowrate.

In addition, another hot-wire sensor S6-E can also be positioned similarly in series with the exhalation flowrate sensor 12 and can in this way permit measurement of the exhaled fraction of xenon by synchronizing the blocking phase with the insufflation phase by detecting a positive insufflation pressure or an insufflation flowrate.

Of course, the hot-wire sensor(s) used in the context of the invention can comprise one or more wires made of any suitable electrically conductive material, in particular platinum.

In all cases, the apparatus of the invention can be used in any circumstance and in any location, in particular in an operating theater, during the anesthesia phases with xenon, in such a way as to improve patient safety, and it falls within the scope of the requirements governing the monitoring of anesthetic gases. In such a gas, the gaseous xenon is always mixed with oxygen on its own, with air, or with oxygen and possibly one or more halogenated compounds and/or with nitrous oxide.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. An apparatus for ventilatory anesthesia of a patient by administration of a gas containing gaseous xenon, said apparatus comprising:
   a main gas circuit (CP) in the form of an open or closed circuit having an inhalation branch (16) for supplying a gaseous mixture containing xenon to the patient and an exhalation branch (18) for conveying the gaseous mixture containing xenon exhaled by the patient, and
   means (S6, M1) for determining the concentration of xenon, which are designed and able to determine the gaseous xenon content in at least part of the main circuit (CP), said means (S6, M1) for determining the concentration of xenon comprising a first hot-wire sensor (S6-E) having a first electrically conductive wire (FC1) in direct contact with at least part of the gaseous flow containing the xenon, wherein:
   the first hot-wire sensor (S6-E) having the first conductive wire (FC1) further comprises a gas-supply main line (LP) having a first bypass line (BP) connected fluidically to said gas-supply main line (LP) upstream and downstream from said first conductive wire (FC1), as seen in the direction of circulation of the gas in the main line (LP), and
   at least a first solenoid valve (EV1) is arranged in the area of the upstream connection of the first bypass line (BP) to said main line (LP) in such a way as to direct the gaseous flow containing the xenon either to the main line (LP), on which said first conductive wire (FC1) is arranged, or to the first bypass line (BP).

2. The apparatus of claim 1, wherein the gas-supply main line (LP) and the first bypass line (BP) are ramifications of a second bypass line (S1, S3, S5) communicating fluidically with the main circuit (CP), and in that the first solenoid valve (EV1) is arranged at the intersection of said second bypass line (S1, S3, S5), the gas-supply main line (LP) and the first bypass line (BP), and the connection of the second bypass line (S1, S3, S5) to the main circuit (CP) is made on the inhalation branch (16) and/or on the exhalation branch (18) and/or at a site located in immediate proximity to the patient's mouth.

3. The apparatus of claim 2, wherein the connection of the second bypass line (S1, S3, S5) to the main circuit (CP) is made in the area of a connection site (17) between the inhalation branch (16) and the exhalation branch (18) of said main circuit (CP).

4. The apparatus of claim 3, wherein at least a second solenoid valve (EV2) is arranged in the area of the downstream connection of the first bypass line (BP) to said main line (LP).

5. The apparatus of claim 4, wherein at least a second sensor with conductive wire (FC2) is arranged on the first bypass line (BP) and measures the xenon concentration, during the exhalation phase, while the first conductive wire (FC1) measures the concentration during the inhalation phase, or vice versa.

6. The apparatus of claim 5, wherein the first and second solenoid valves (EV1, EV2) are controlled by control means (3) or by an independent interface.

7. The apparatus of claim 3, wherein at least one nonreturn valve (CR) is arranged on the gas-supply main line (LP), between the first conductive wire (FC1) and a downstream connection of the first bypass line (BP) to said main line (LP).

8. The apparatus of claim 7, wherein at least a second sensor with conductive wire (FC2) is arranged on the first bypass line (BP) and measures the xenon concentration, during the exhalation phase, while the first conductive wire (FC1) measures the concentration during the inhalation phase, or vice versa.

9. The apparatus of claim 2, wherein the connection of the second bypass line (S1, S3, S5) to the main circuit (CP) is made in the area of a Y-shaped connector piece or of a bacteriological filter arranged on the main circuit (CP).

10. The apparatus of claim 2, wherein at least a second solenoid valve (EV2) is arranged in the area of the downstream connection of the first bypass line (BP) to said main line (LP).

11. The apparatus of claim 10, wherein at least a second sensor with conductive wire (FC2) is arranged on the first bypass line (BP) and measures the xenon concentration, during the exhalation phase, while the first conductive wire (FC1) measures the concentration during the inhalation phase, or vice versa.

12. The apparatus of claim 11, wherein the first and second solenoid valves (EV1, EV2) are controlled by control means (3) or by an independent interface.

13. The apparatus of claim 2, wherein at least one nonreturn valve (CR) is arranged on the gas-supply main line (LP), between the first conductive wire (FC1) and a downstream connection of the first bypass line (BP) to said main line (LP).

14. The apparatus of claim 13, wherein at least a second sensor with conductive wire (FC2) is arranged on the first bypass line (BP) and measures the xenon concentration, during the exhalation phase, while the first conductive wire (FC1) measures the concentration during the inhalation phase, or vice versa.

15. The apparatus of claim 14, wherein the first and second solenoid valves (EV1, EV2) are controlled by control means (3) or by an independent interface.

16. The apparatus of claim 1, wherein the first hot-wire sensor is arranged directly on the inhalation (16) or exhalation (18) branch of the main circuit (CP), and in that the gas-supply main line (LP) and the bypass line (BP) are ramifications of the inhalation (16) or exhalation (18) branch of the main circuit (CP), and in that the first solenoid valve (EV1) is arranged at the intersection of the inhalation (16) or exhalation (18) branch, the main line (LP) and the first bypass line (BP).

17. The apparatus of claim 16, wherein the first hot-wire sensor is arranged on the inhalation branch (16), upstream or downstream from an inhalation flowrate sensor (11), so as to permit measurement of the inhaled fraction of xenon.

18. The apparatus of claim 16, wherein the first hot-wire sensor is arranged on the exhalation branch (18), upstream or downstream from an exhalation flowrate sensor (12), so as to permit measurement of the exhaled fraction of xenon.

19. The apparatus of claim 1, wherein at least a second solenoid valve (EV2) is arranged in the area of the downstream connection of the first bypass line (BP) to said main line (LP).

20. The apparatus of claim 19, wherein the first and second solenoid valves (EV1, EV2) are controlled by control means (3) or by an independent interface.

21. The apparatus of claim 1, wherein at least one nonreturn valve (CR) is arranged on the gas-supply main line (LP), between the first conductive wire (FC1) and the downstream connection of the first bypass line (BP) to said main line (LP).

22. The apparatus of claim 1, wherein at least a second sensor with conductive wire (FC2) is arranged on the first bypass line (BP) and measures the xenon concentration during the exhalation phase while the first conductive wire (FC1) measures the concentration during the inhalation phase, or vice versa.

* * * * *

UNITED STATES PATENT AND TRADEMARK OFFICE
CERTIFICATE OF CORRECTION

| | | |
|---|---|---|
| PATENT NO. | : 8,870,784 B2 | Page 1 of 1 |
| APPLICATION NO. | : 12/994022 | |
| DATED | : October 28, 2014 | |
| INVENTOR(S) | : Richard Blandin et al. | |

It is certified that error appears in the above-identified patent and that said Letters Patent is hereby corrected as shown below:

On the Title Page, Item (54) and in the Specification, Column 1, lines 1-3, PRECISION OF XENON CONTENT MEASUREMENT IN A VENTILATORY ANESTHESIA APPARATUS Insert -- IMPROVEMENT IN THE -- before the word PRECISION.

Signed and Sealed this
Seventeenth Day of February, 2015

Michelle K. Lee
*Deputy Director of the United States Patent and Trademark Office*